(12) United States Patent
Gates et al.

(10) Patent No.: US 11,801,109 B2
(45) Date of Patent: Oct. 31, 2023

(54) CONTAINER FOR MEDICAL ITEMS AND DISPOSABLE WASTE

(71) Applicants: Juliana Elizabeth Gates, Mineral Wells, TX (US); Rhonda Kay Huddleston, Mineral Wells, TX (US)

(72) Inventors: Juliana Elizabeth Gates, Mineral Wells, TX (US); Rhonda Kay Huddleston, Mineral Wells, TX (US)

( * ) Notice: Subject to any disclaimer, the term of this patent is extended or adjusted under 35 U.S.C. 154(b) by 110 days.

(21) Appl. No.: 17/172,182

(22) Filed: Feb. 10, 2021

(65) Prior Publication Data

US 2021/0244492 A1  Aug. 12, 2021

Related U.S. Application Data

(60) Provisional application No. 62/972,536, filed on Feb. 10, 2020.

(51) Int. Cl.
| | |
|---|---|
| *A61B 50/36* | (2016.01) |
| *A45C 3/00* | (2006.01) |
| *A45C 13/02* | (2006.01) |
| *A45C 13/10* | (2006.01) |
| *A61B 50/30* | (2016.01) |

(52) U.S. Cl.
CPC ............. *A61B 50/36* (2016.02); *A45C 3/001* (2013.01); *A45C 13/02* (2013.01); *A45C 13/1046* (2013.01); *A61B 2050/3008* (2016.02); *A61B 2050/314* (2016.02)

(58) Field of Classification Search
CPC ...... A61B 2050/314; A61B 2050/3008; A61B 50/36; A45C 3/02; A45C 3/001; A45C 3/00; A45C 13/1046; A45C 9/00

USPC ............................. 383/4, 71, 40, 72; 206/570
See application file for complete search history.

(56) References Cited

U.S. PATENT DOCUMENTS

| | | | | |
|---|---|---|---|---|
| 2,479,203 | A * | 8/1949 | Brown | A47D 15/003 383/4 |
| 4,337,812 | A * | 7/1982 | Trinkner | A45F 4/02 206/541 |
| 4,777,992 | A * | 10/1988 | Olger | A47G 11/003 206/541 |
| 4,930,635 | A * | 6/1990 | Hotchkiss | A45C 11/16 206/495 |
| 4,955,068 | A * | 9/1990 | Tennihan | B65B 67/12 52/165 |
| 5,092,681 | A * | 3/1992 | Ashley, III | B65D 33/28 383/4 |

(Continued)

*Primary Examiner* — Chun Hoi Cheung
(74) *Attorney, Agent, or Firm* — Edwin S. Flores; Daniel J. Chalker; Chalker Flores, LLP

(57) ABSTRACT

A container has a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches.

18 Claims, 6 Drawing Sheets

(56) References Cited

U.S. PATENT DOCUMENTS

| | | | | |
|---|---|---|---|---|
| 5,195,828 | A | * | 3/1993 | Bush-Rodriquez ...... A45C 9/00 |
| | | | | 383/4 |
| RE34,849 | E | * | 2/1995 | Sanders ................ B65F 1/0006 |
| | | | | 383/7 |
| 5,425,468 | A | | 6/1995 | Birkel et al. |
| 5,895,118 | A | * | 4/1999 | Hensley ................... A45C 9/00 |
| | | | | 383/117 |
| 5,971,611 | A | * | 10/1999 | Rosengren ............... A45C 9/00 |
| | | | | 383/14 |
| 6,267,504 | B1 | * | 7/2001 | Screen ................... B65D 29/04 |
| | | | | 383/117 |
| 7,520,010 | B2 | * | 4/2009 | Welch .................... A47D 5/006 |
| | | | | 5/655 |
| 7,594,754 | B2 | * | 9/2009 | Costello ................... B65F 1/00 |
| | | | | 383/117 |
| 7,785,008 | B2 | * | 8/2010 | Schoenig ............ A45C 13/002 |
| | | | | 383/4 |
| 8,371,448 | B1 | | 2/2013 | Reaux |
| 8,642,870 | B1 | * | 2/2014 | Rosa ...................... G10H 1/348 |
| | | | | 84/453 |
| 8,905,988 | B2 | | 12/2014 | Ung et al. |
| 9,084,459 | B2 | * | 7/2015 | Fazackerley ....... A45C 13/1046 |
| 2017/0303652 | A1 | * | 10/2017 | Tate .......................... A45C 3/00 |
| 2019/0269210 | A1 | * | 9/2019 | Melamed ............... A45C 13/02 |
| 2019/0343256 | A1 | * | 11/2019 | Portillo ................... A45C 3/00 |
| 2021/0061522 | A1 | * | 3/2021 | Bertrand ............... B65D 51/12 |

\* cited by examiner

CONTAINER FOR MEDICAL ITEMS AND DISPOSABLE WASTE

CROSS-REFERENCE TO RELATED APPLICATIONS

Not applicable.

STATEMENT OF FEDERALLY FUNDED RESEARCH

Not applicable.

TECHNICAL FIELD OF THE INVENTION

The present invention relates in general to the field of disposable waste containment and transportation, and more particularly, to a container for storing and transporting disposable waste in a separate compartment from other items.

BACKGROUND OF THE INVENTION

Without limiting the scope of the invention, its background is described in connection with disposable medical waste.

In caring for patients, the need often arises to carry items used in patient care, such as clean scissors and clean bandages, and/or contaminated items, such as used scissors and used bandages. It is often difficult for a caregiver to carry these items at once safely, without cross-contamination. There is a need for a container in which medical waste and/or non-waste items can conveniently be carried in a way that prevents cross-contamination, and further, that the container occupies a small volume in its stored and/or unused state so that many such containers can be stored or transported together, and that the container itself be disposable after a number of uses.

U.S. Pat. No. 5,425,468, issued to Birkel et al., is said to disclose a receptacle for collecting body secretions or medical waste, including an outer rigid open-top container and an inner flexible, transparent bag or liner. The open top of the bag can be closed by a rib and groove type connection that extends the full width of the bag side tabs extend outwardly from opposite sides of the bag and are provided with finger holes. The bag has a size such that the upper portion of the bag drapes downwardly over the upper end of the container and the side tabs are located between the container and the downwardly hanging upper edge portion of the bag. After receiving secretions, the operator grasps the side tabs, pulling upwardly and outwardly to remove the bag from the container. The bag can then be closed through operation of the rib and groove connection.

U.S. Pat. No. 8,371,448, issued to Reaux, is said to disclose a storage system for storing used surgical towels, sponges or other medical waste materials that includes a rear panel having an upper portion and a lower portion formed from a flexible sheet material. The upper portion of the rear panel has a coupling mechanism for coupling the device to a sterile structure of a surgical room. In certain embodiments, the rear panel may have a weakened partition area for separating the lower portion from the upper portion. A compartment assembly is formed by two or more flexible compartments provided on the lower portion of the rear panel. Each compartment may be liquid impervious and have an upper opening for introducing materials into the compartment. Each compartment has a forward wall that is at least partially transparent so that the contents of the compartment are observable. All components of the storage device may be sterile for use in a sterile environment. In certain embodiments, a storage system may be provided by coupling at least two storage devices together.

U.S. Pat. No. 8,905,988, issued to Ung et al., is said to disclose a disposal-bag system attached to or formed at least partially by a disposable object (e.g., a diaper) includes a container that houses a disposal bag folded into a compact arrangement. The container is generally thin and flat and sized for storing the bag, and the bag is sized for holding the disposable object that the system is used with. And the bag is at least partially removable from the container so that the disposable object can be placed into it for disposal. In use, the container is opened, the bag is extended from the container and opened, the disposable object is grasped by reaching through the bag, the bag is inverted to now hold the disposable object, and the bag is closed and disposed of. In this way, the disposal-bag system provides a convenient, sanitary, and self-contained method of disposing of soiled diapers or other disposable objects.

SUMMARY OF THE INVENTION

In one embodiment, a container comprises: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches. In one aspect, the sheet has a circular shape, an elliptical shape, or an ovoid shape. In another aspect, one of the one or more first flexible materials is an anti-microbial and forms the first side of the sheet. In another aspect, one of the one or more first flexible materials is a water-resistant paper or cloth and forms a second side of the sheet. In another aspect, the seam around the circumference is sewn or glued. In another aspect, the cinch tie comprises cloth, plastic, polymer, or some combination. In another aspect, the barrier flap is secured to the first side of the sheet along a line including the center of the sheet with a sewn seam or a glued seam. In another aspect, the barrier flap is configured to be further secured at a location on the first side of the sheet proximal to the circumference with a snap fastener, an adhesive fastener, or a hook-and-loop fastener.

In another embodiment, a kit comprises: one or more items used by a caregiver in caring for a patient; and a container comprising: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches. In one aspect, the sheet has a circular shape, an elliptical shape, or an ovoid shape. In another aspect, one of the one or more first flexible materials is an anti-microbial and forms the first side of the sheet of one or more first flexible materials. In another aspect, one of the one or more first flexible materials is a water-resistant paper or cloth and forms a second side of the sheet. In another aspect, the seam around the circumference is sewn or glued. In another aspect, the cinch tie comprises cloth, plastic, polymer, or some combination. In another aspect, the barrier flap is secured to the first side of the sheet along a line including the center of the sheet with a sewn seam or a glued seam. In another aspect, the barrier flap is configured to be further secured at a location on the first side of the sheet proximal to the circumference with a snap fastener, an adhesive fastener, or a hook-and-loop fastener. In one aspect, the sheet has a circular shape, an elliptical shape, or an ovoid shape. In another aspect, one of the one or more first flexible materials is an anti-microbial and forms the first side of the sheet of one or more first flexible materials. In another aspect, one of the one or more first flexible materials is a water-resistant paper or cloth and forms a second side of the sheet. In another aspect, the seam around the circumference is sewn or glued. In another aspect, the cinch tie comprises cloth, plastic, polymer, or some combination. In another aspect, the barrier flap is secured to the first side of the sheet along a line including the center of the sheet with a sewn seam or a glued seam. In another aspect, the barrier flap is configured to be further secured at a location on the first side of the sheet proximal to the circumference with a snap fastener, an adhesive fastener, or a hook-and-loop fastener.

In one embodiment a method of separating items in a container comprises: providing a first item and a second item; providing a container comprising: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches; placing the first item on the sheet on a first side of the barrier flap; placing the second item on a second side of the barrier flap; securing the barrier flap at the location on the first side of the sheet proximal to the circumference; and pulling the cinch tie out through the at least two notches to draw the seam around the circumference shut. In one aspect, the sheet has a circular shape, an elliptical shape, or an ovoid shape. In another aspect, one of the one or more first flexible materials is an anti-microbial and forms the first side of the sheet of one or more first flexible materials. In another aspect, one of the one or more first flexible materials is a water-resistant paper or cloth and forms a second side of the sheet of one or more first flexible materials. In another aspect, the seam around the circumference is sewn or glued. In another aspect, the cinch tie comprises cloth, plastic, polymer, or some combination. In another aspect, the barrier flap is secured to the first side of the sheet along a line including the center of the sheet with a sewn seam or a glued seam. In another aspect, the barrier flap is configured to be further secured at a location on the first side of the sheet proximal to the circumference with a snap fastener, an adhesive fastener, or a hook-and-loop fastener.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1:
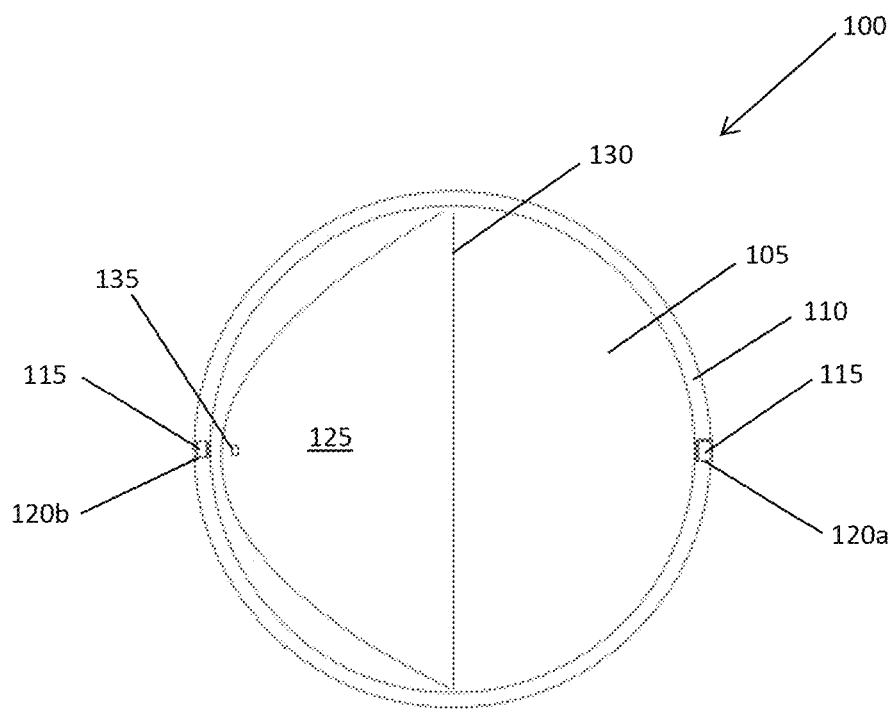
FIG. 1 shows a top view of a container.

FIG. 1 shows an embodiment of the present invention, a container 100 that includes a sheet 105 of one or more first flexible materials; a seam 110 around a circumference of the sheet 105; a cinch tie 115 enclosed within the seam 110 and exposed at each of at least two notches 120a, 120b in the seam on opposite sides of the sheet; and a barrier flap 125 of a second flexible material secured to a first side of the sheet (the side shown in FIG. 1) along a line 130 that includes the center of the sheet, wherein the barrier flap 125 is configured to divide an interior space of the container into a first compartment and a second compartment when the container 100 is closed and is configured to be further secured at a location 135 on the first side of the sheet proximal to the circumference; wherein the cinch tie 115 is configured to close the container 100 by drawing the seam 110 around the circumference shut when pulled out through the at least two notches 120*a*, 120*b*. The barrier flap 125 separates items on one side of the barrier flap 125 from items on the other side of the barrier flap 125, preventing cross-contamination. The sheet 105 may have a circular shape, an elliptical shape, or an ovoid shape. One of the one or more first flexible materials may be an anti-microbial forming the first side of the sheet 105. One of the one or more first flexible materials may be a water-resistant paper or cloth forming a second side of the sheet. The seam 110 around the circumference may be, for example, sewn or glued. The cinch tie 115 comprises, for example, cloth, plastic, polymer, or some combination. The barrier flap 125 may be secured to the first side of the sheet 105 along a line 130 including the center of the sheet with, for example, a sewn seam or a glued seam. The barrier flap 125 may be configured to be further secured at a location on the first side of the sheet 105 proximal to the circumference with, for example, a snap fastener, an adhesive fastener, or a hook-and-loop fastener.

As used herein, "side of the sheet 105" refers to the entire surface of the sheet 105 that faces in a particular direction. The first side of the sheet 105 faces the viewer in FIGS. 1-5, while the second side of the sheet faces away from the viewer and is not visible in FIGS. 1-5.

When not in use, the container 100 stores flat, and the container 100 is itself disposable.

Figure 2:
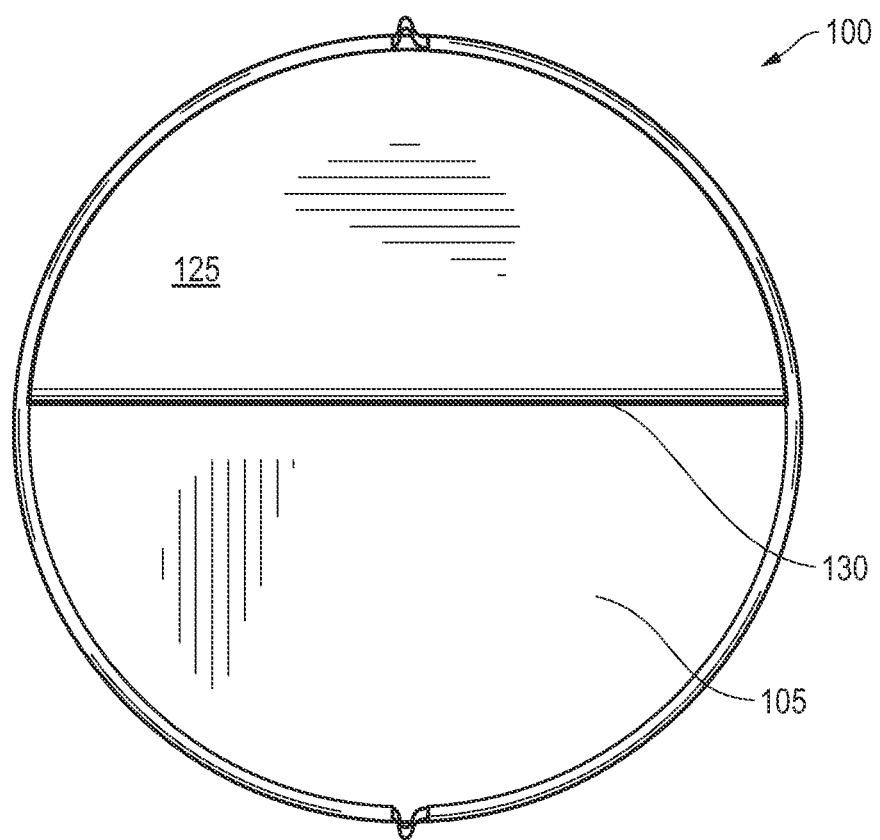
FIG. 2 shows a top view of the container with the barrier flap positioned to side of the line.

FIG. 2 shows a top view of the container 100 with the barrier flap 125 positioned to side of the line 130.

Figure 3:
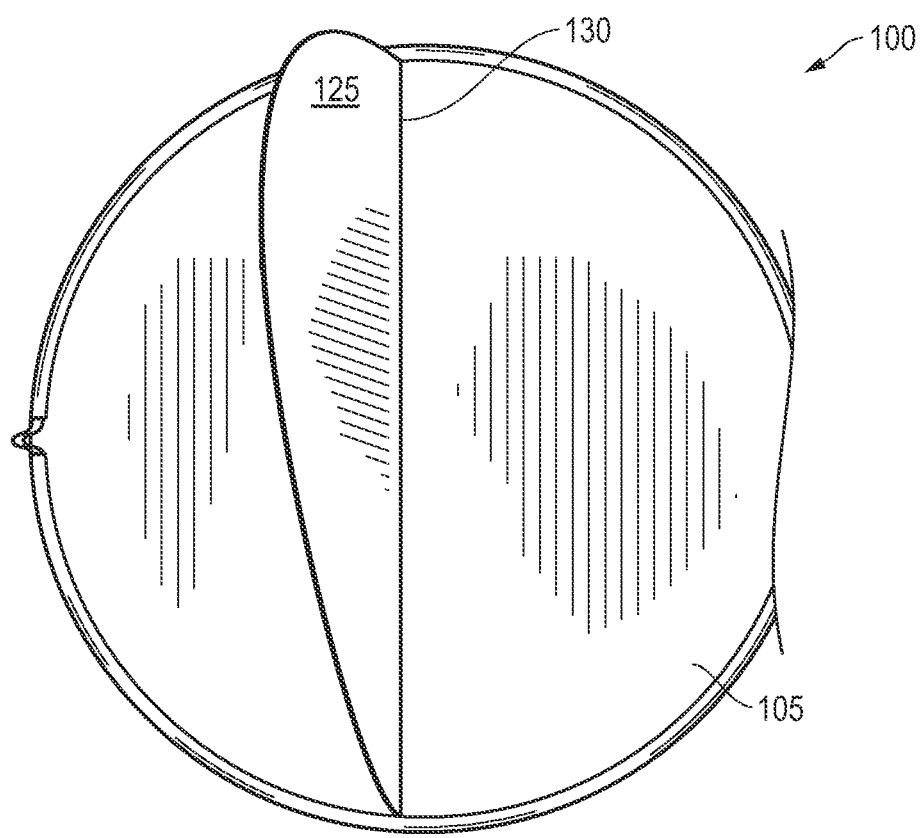
FIG. 3 shows the container with the barrier flap positioned above the first surface of the sheet, toward the viewer.

FIG. 3 shows the container 100 with the barrier flap 125 positioned above the first surface of the sheet 105, toward the viewer.

Figure 4:
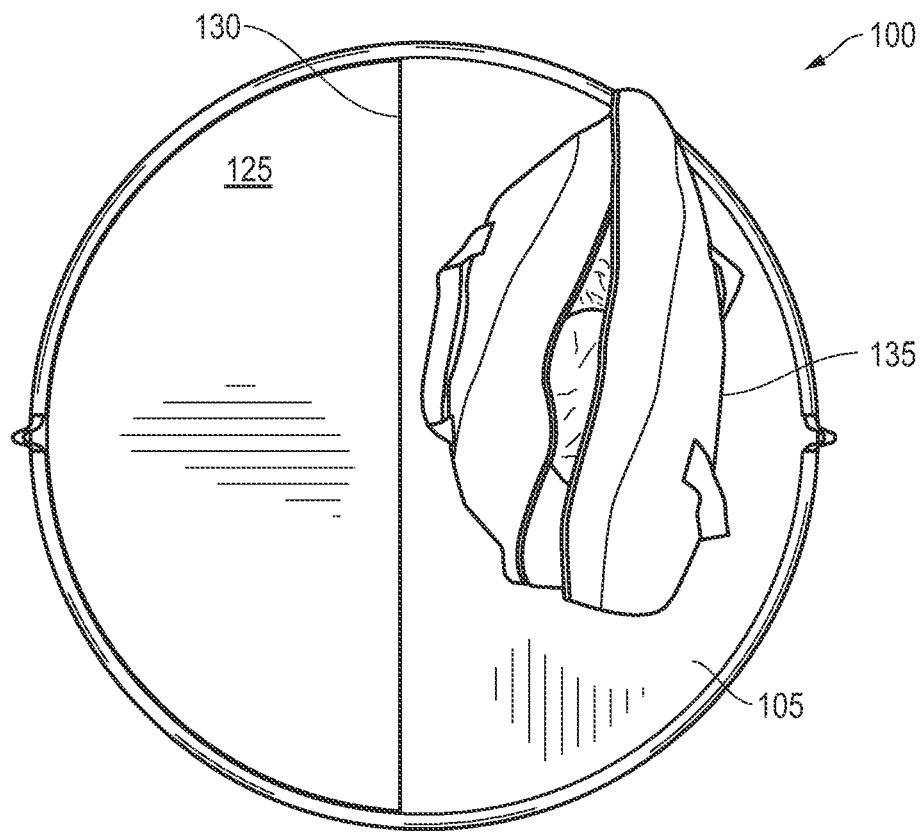
FIG. 4 shows the container with the barrier flap positioned to the right of the line and a smaller container containing medical waste to the right of the line, on the first side of the sheet 105.

FIG. 4 shows the container 100 with the barrier flap 125 positioned to the right of the line 130 and an item 135 to the right of the line 130, on the first side of the sheet 105. Item 135 may be clean or contaminated by use with a patient.

Figure 5:
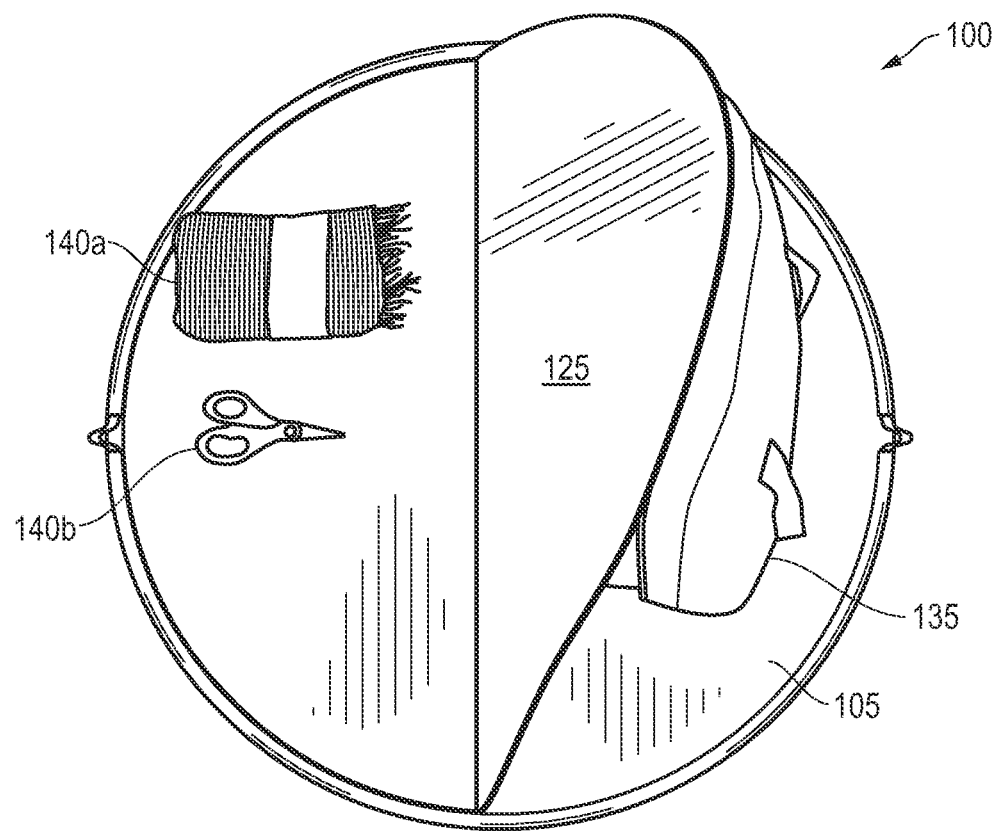
FIG. 5 shows the container with the barrier flap positioned above the first surface of the sheet, with the smaller container containing medical waste to the right of the line and non-waste items to the left of the line.

FIG. 5 shows the container 100 with the barrier flap 125 positioned above the first surface of the sheet 105, with the item 135 to the right of the line 130 and additional items 140*a*, 140*b* to the left of the line 130. Items 140*a*, 140*b* may be clean or contaminated by use with a patient.

Figure 6:
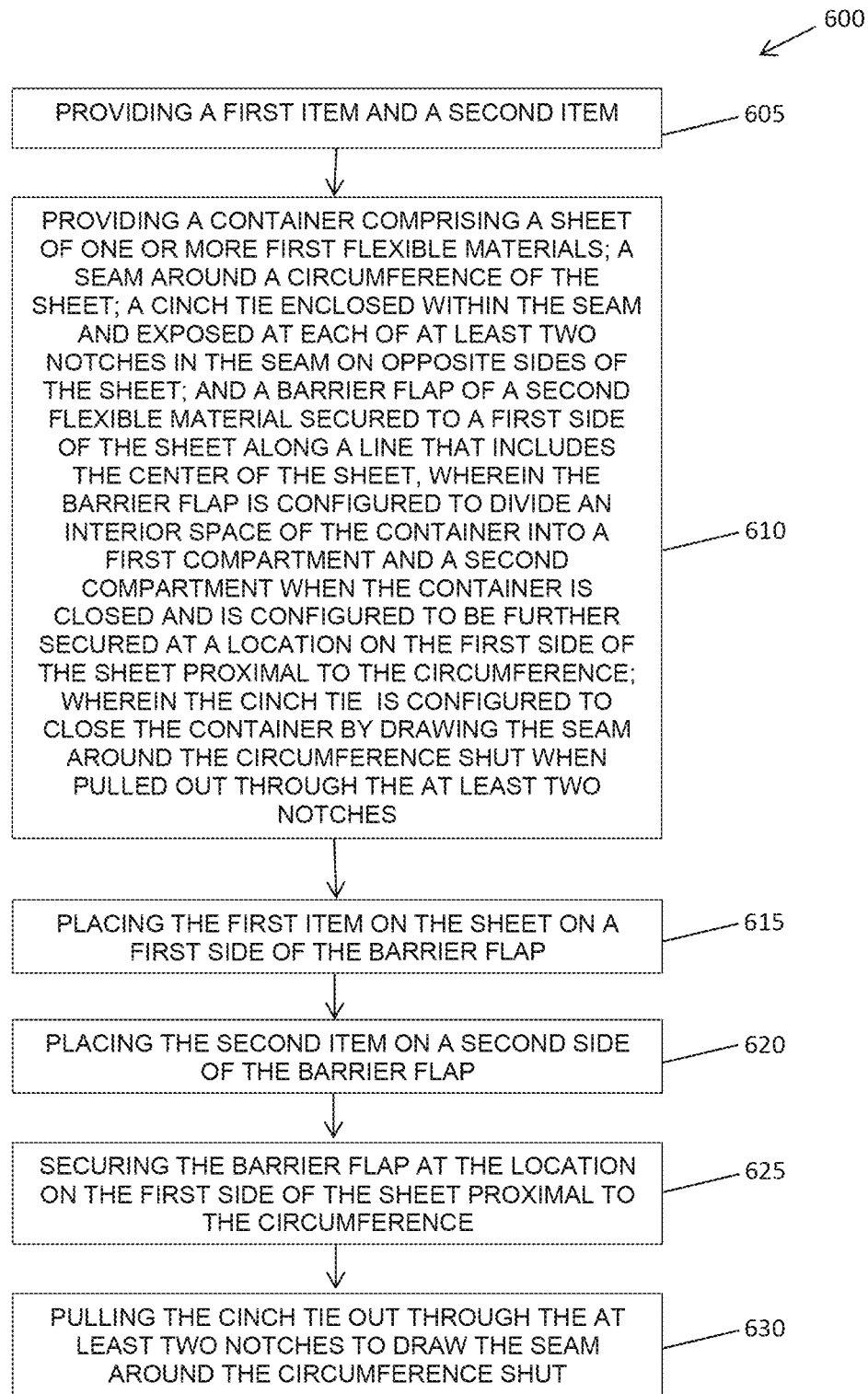
FIG. 6 shows a method of separating waste material from non-waste material in a container.

FIG. 6 shows a method 600 of separating items in a container. Block 605 of method 600 includes providing a first item and a second item. Block 610 includes providing a container including a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed and is configured to be further secured at a location on the first side of the sheet proximal to the circumference; wherein the cinch tie is configured to close the container by drawing the seam around the circumference shut when pulled out through the at least two notches. Included in block 615 is placing the first item on the sheet on a first side of the barrier flap, and in block 620, placing the second item on a second side of the barrier flap. Block 625 includes securing the barrier flap at the location on the first side of the sheet proximal to the circumference. Block 630 includes pulling the cinch tie out through the at least two notches to draw the seam around the circumference shut.

In one embodiment, a container comprises, consists essentially of, or consists of: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches.

In another embodiment, a kit comprises, consists essentially of, or consists of: one or more items used by a caregiver in caring for a patient; and a container comprising: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches.

In one embodiment a method of separating items in a container comprises, consists essentially of, or consists of: providing a first item and a second item; providing a container comprising: a sheet of one or more first flexible materials; a seam around a circumference of the sheet; a cinch tie enclosed within the seam and exposed at each of at least two notches in the seam on opposite sides of the sheet; and a barrier flap of a second flexible material secured to a first side of the sheet along a line that includes the center of the sheet, wherein the barrier flap is configured to divide an interior space of the container into a first compartment and a second compartment when the container is closed, and wherein the barrier flap is configured to be further secured at a location on the first side of the sheet proximal to the circumference; wherein the cinch tie is configured to close the container by drawing the seam shut when pulled out through the at least two notches; placing the first item on the sheet on a first side of the barrier flap; placing the second item on a second side of the barrier flap; securing the barrier flap at the location on the first side of the sheet proximal to the circumference; and pulling the cinch tie out through the at least two notches to draw the seam around the circumference shut.

It can be seen that the container 100 and the method 600 provide a container and a method by which medical waste and/or non-waste items can conveniently be carried in a way that prevents cross-contamination, and further, that the container occupies a small volume in its stored and/or unused state so that many can be stored or transported together, and that the container itself be disposable after a number of uses.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

To aid the Patent Office, and any readers of any patent issued on this application in interpreting the claims appended hereto, applicants wish to note that they do not intend any of the appended claims to invoke 35 U.S.C. § 112(f) as it exists on the date of filing hereof unless the words "means for" or "step for" are explicitly used in the particular claim.

What is claimed is:

1. A container for a medical waste comprising:
    a sheet of one or more first flexible medical waste barrier materials, wherein one of the one or more first flexible medical waste barrier materials is anti-microbial and water-resistant;
    a seam around a circumference of the sheet;
    a cinch tie enclosed within the seam and exposed at each of at least two notches in the seam on opposite sides of the sheet; and
    a barrier flap of a second flexible material secured to a first side of the sheet along a line that includes the center of the sheet, wherein the barrier flap is configured to divide an interior space of the container into a first compartment having a first medical waste and a second compartment having a second medical waste when the container is closed, and wherein the barrier flap is configured to be further secured at a location on the first side of the sheet proximal to the circumference;
    wherein the cinch tie is configured to close the container by drawing the seam shut when pulled out through the at least two notches for the first and second medical waste; and
    wherein the barrier flap is secured to the first side of the sheet along a line including the center of the sheet with a glued seam.

2. The container of claim 1, wherein the sheet has a circular shape, an elliptical shape, or an ovoid shape.

3. The container of claim 1, wherein one of the one or more first flexible materials is a water-resistant paper or cloth and forms a second side of the sheet.

4. The container of claim 1, wherein the seam around the circumference is sewn or glued.

5. The container of claim 1, wherein the cinch tie comprises cloth, plastic, polymer, or some combination.

6. The container of claim 1, wherein the barrier flap is configured to be further secured at a location on the first side of the sheet proximal to the circumference with a snap fastener, an adhesive fastener, or a hook-and-loop fastener.

7. A kit for containing a medical waste comprising:
one or more items used by a caregiver in caring for a patient; and
a container comprising:
   a sheet of one or more first flexible medical waste barrier materials, wherein one of the one or more first flexible medical waste barrier materials is anti-microbial and water-resistant;
   a seam around a circumference of the sheet;
   a cinch tie enclosed within the seam and exposed at each of at least two notches in the seam on opposite sides of the sheet; and
   a barrier flap of a second flexible material secured to a first side of the sheet along a line that includes the center of the sheet of first flexible material, wherein the barrier flap is configured to divide an interior space of the container into a first compartment capable of storing a first medical waste and a second compartment capable of storing a second medical waste when the container is closed, and wherein the barrier flap is configured to be further secured at a location on the first side of the sheet proximal to the circumference;
   wherein the cinch tie is configured to close the container by drawing the seam shut when the cinch tie is pulled out through the at least two notches, thereby storing the first and second medical waste; and
   wherein the barrier flap is secured to the first side of the sheet along a line including the center of the sheet with a glued seam.

8. The kit of claim 7, wherein the sheet has a circular shape, an elliptical shape, or an ovoid shape.

9. The kit of claim 7, wherein one of the one or more first flexible materials is a water-resistant paper or cloth and forms a second side of the sheet.

10. The kit of claim 7, wherein the seam around the circumference is sewn or glued.

11. The kit of claim 7, wherein the cinch tie comprises cloth, plastic, polymer, or some combination.

12. The kit of claim 7, wherein the barrier flap is configured to be further secured at a location on the first side of the sheet proximal to the circumference with a snap fastener, an adhesive fastener, or a hook-and-loop fastener.

13. A method of separating items of medical waste in a container comprising:
providing a first item and a second item;
providing a container comprising:
   a sheet of one or more first flexible medical waste barrier materials, wherein one of the one or more first flexible medical waste barrier materials is anti-microbial and water-resistant;
   a seam around a circumference of the sheet;
   a cinch tie enclosed within the seam and exposed at each of at least two notches in the seam on opposite sides of the sheet; and
   a barrier flap of a second flexible material secured to a first side of the sheet along a line that includes the center of the sheet, wherein the barrier flap is configured to divide an interior space of the container into a first compartment for storing a first medical waste and a second compartment for storing a second medical waste when the container is closed, and wherein the barrier flap is configured to be further secured at a location on the first side of the sheet proximal to the circumference;
   wherein the cinch tie is configured to close the container by drawing the seam shut when pulled out through the at least two notches; and
   wherein the barrier flap is secured to the first side of the sheet along a line including the center of the sheet with a glued seam;
placing the first item on the sheet on a first side of the barrier flap;
placing the second item on a second side of the barrier flap;
securing the barrier flap at the location on the first side of the sheet proximal to the circumference; and
pulling the cinch tie out through the at least two notches to draw the seam around the circumference shut to store the first and second medical waste.

14. The method of claim 13, wherein the sheet has a circular shape, an elliptical shape, or an ovoid shape.

15. The method of claim 13, wherein one of the one or more first flexible materials is a water-resistant paper or cloth and forms a second side of the sheet of one or more first flexible materials.

16. The method of claim 13, wherein the seam around the circumference is sewn or glued.

17. The method of claim 13, wherein the cinch tie comprises cloth, plastic, polymer, or some combination.

18. The method of claim 13, wherein the barrier flap is configured to be further secured at a location on the first side of the sheet proximal to the circumference with a snap fastener, an adhesive fastener, or a hook-and-loop fastener.

* * * * *